US005795882A

United States Patent [19]
Bishop et al.

[11] Patent Number: 5,795,882
[45] Date of Patent: Aug. 18, 1998

[54] METHOD OF TREATING PROSTATIC DISEASES USING DELAYED AND/OR SUSTAINED RELEASE VITAMIN D FORMULATIONS

[75] Inventors: Charles W. Bishop; Joyce C. Knutson, both of Madison; Charles R. Valliere, Waunakee, all of Wis.

[73] Assignee: Bone Care International, Inc., Madison, Wis.

[21] Appl. No.: 775,447

[22] Filed: Dec. 30, 1996

Related U.S. Application Data

[60] Continuation-in-part of Ser. No. 485,354, Jun. 7, 1995, Pat. No. 5,614,513, which is a division of Ser. No. 196,116, Feb. 22, 1994, Pat. No. 5,529,991, which is a continuation-in-part of Ser. No. 901,886, filed as PCT/US93/59612 Jan. 6, 1994, abandoned.

[51] Int. Cl.$^6$ ........................................................ A01N 45/00
[52] U.S. Cl. ............................................................... 514/170
[58] Field of Search ................................................. 514/170

[56] References Cited

U.S. PATENT DOCUMENTS

| | | |
|---|---|---|
| 2,216,719 | 10/1940 | Boer . |
| 2,434,015 | 1/1948 | Rosenberg et al. . |
| 4,230,701 | 10/1980 | Holick et al. . |
| 4,335,120 | 6/1982 | Holick et al. . |
| 4,391,802 | 7/1983 | Suda et al. . |
| 4,505,906 | 3/1985 | DeLuca et al. . |
| 4,539,153 | 9/1985 | Vandewalle et al. . |
| 4,684,524 | 8/1987 | Eckenhoff et al. . |
| 4,728,643 | 3/1988 | Holick et al. . |
| 5,013,728 | 5/1991 | Grodberg . |
| 5,372,996 | 12/1994 | Labrie . |

FOREIGN PATENT DOCUMENTS

| | | |
|---|---|---|
| 649802 | 2/1994 | Australia . |
| 650286 | 6/1994 | Australia . |
| 0 070 588 | 1/1983 | European Pat. Off. . |
| 0 215 956 | 4/1987 | European Pat. Off. . |
| 0 306 236 | 3/1989 | European Pat. Off. . |
| S59-10562 | 1/1984 | Japan . |
| WO 84/04527 | 9/1984 | WIPO . |
| WO 90/09179 | 8/1990 | WIPO . |
| WO 92/09271 | 6/1992 | WIPO . |

OTHER PUBLICATIONS

Miller et al., "The Human Prostatic Carcinoma Cell Line LNCaP Expresses Biologically Active, Specific Receptors for 1α,25-Dihydroxyvitamin $D_3$," 52 *Cancer Res.* (1992) 515–520.

K. Lehmann, D. Dreher, "Coating of Tablets and Small Particles With Acrylic resins by fluid Bed Technology," *Int. J. Pharm. Tech. & Prod. Mfr.* 2(4), 31–43 (1981).

Skowronski et al., "Actions of Vitamin $D_3$ Analogs on Human Prostate Cancer Cell Lines: Comparison with 1,25-Dihydroxyvitamin $D_3$," 136 *Endocrinology* (1995) 20–26.

Skowronski et al., "Vitamin D and Prostate Cancer: 1,25 Dihydroxyvitamin $D_3$ Receptors and Actions in Human Prostate Cancer Cell Lines," 132 *Endocrinology* (1993) 1952–1960.

*Transactions of the Association of American Physicians,* vol. XCII, 1979, pp. 54–63, M. F. Holick, S. C. McNeill, J. A. MacLaughlin, S. A. Holick, M. B. Clark and J. T. Potts, Jr., "Physiologic Implications of the Formation of Previtamin D in Skin".

*Chemical Abstracts,* vol. 110, No. 10, 1989, Columbus, Ohio, Abstract No. 84136v, M. Takahashi, H. Mochizuki, "Enteric–Soluble Capsule Base Composed of Poly(Ethylene Glycol) or Its Substitutes and Cellulose Acetate Phthalate or Hydroxypropyl Methyl Cellulose Phthalate".

*Harrison's Principles of Internal Medicine*: Part Eleven, "Disorders of Bone & Mineral Metabolism," Chapter 335, E. Braunwald et al. (eds.) McGraw–Hill, New York (1987) pp. 1860–1865.

M. L. Curtin and W. H. Okamura, *J. Am. Chem. Soc.,* vol. 113 (1991) pp. 6958–6966.

CA 116:254522 1991.
CA 115:278633 1990.
CA 116:75862 1991.
CA 110:107718 1988.

Schwartz et al., *Anticancer Res. J.* (1994), 14:1077–81.

Skowronski et al., *Proc. Workshop Vitamin D* (1994), 9th (Vit. D), 520–521.

Miller et al., *Clinical Cancer Res.* (1995), 1(9): 997–1003.

Hsieh et al., *Biochem. Biophys. Res. Commun.* (1996), 223(1), 141–146.

Helund et al., *J. Steroid Biochem. Molec. Biol.* (1996), 58(3): 277–288.

CA 121:292155 (1994).
CA 123:161606 (1994).
CA 123:276705 (1995).
CA 125:49987 (1996).
CA 125:293950 (1996).

*Primary Examiner*—Paul J. Killos
*Attorney, Agent, or Firm*—Teresa J. Welch; Stroud, Stroud, Willink, Thompson & Howard

[57] ABSTRACT

Method of treating prostatic conditions such as prostate cancer and hyperplasia by administering 1α-hydroxyprevitamin D or activated vitamin D or a combination thereof in a sustained release form or a delayed and sustained release formulation. Both the sustained release form and the delayed, sustained release form deliver increased active vitamin D blood levels without significant risk of hypercalcemia associated with other oral dosing of vitamin D forms, to provide the beneficial effect to the diseased prostate tissue.

24 Claims, 2 Drawing Sheets

METHOD OF TREATING PROSTATIC DISEASES USING DELAYED AND/OR SUSTAINED RELEASE VITAMIN D FORMULATIONS

CROSS-REFERENCE TO RELATED APPLICATIONS

This application is a continuation-in-part of Ser. No. 08/485,354, Jun. 7, 1995, now U.S. Pat. No. 5,614,513 which is a divisional of Ser. No. 08/196,116, Feb. 22, 1994, now U.S. Pat. No. 5,529,991, which is a 371(a) of PCT/US93/059612, Jan. 6, 1994, which is a continuation-in-part of Ser. No. 07/901,886, filed as PCT/US93/59612 Jan. 6, 1994, now abandoned, and all of which are incorporated herein by reference.

STATEMENT REGARDING FEDERALLY SPONSORED RESEARCH OR DEVELOPMENT

Not Applicable

BACKGROUND OF THE INVENTION

This invention relates generally to a method of treating hyperproliferative prostatic diseases, and in particular, to the use of delayed and/or sustained release oral medicaments that deliver an active vitamin D compound and, more specifically, to delayed and/or sustained release activated vitamin D or oral 1α-hydroxyprevitamin D, to inhibit the hyperproliferative cellular activity of these diseases and promote cell differentiation.

The prostate gland is found exclusively in male mammals and is subject to certain proliferative diseases. A proliferation of basal and stroma cells of the prostate gland gives rise to benign prostatic hyperplasia which is one common prostate disease. Another common prostate disease is prostate cancer, especially prostatic adenocarcinoma. Both prostatic hyperplasia and prostate cancer have a high rate of incidence in the aging human male population. Approximately one out of every four males above the age of 55 suffers from a prostate disease of some form or another.

Prostate cancer is currently the second most frequent cause of cancer death after lung cancer among American males. Mortality rates for prostate cancer increase logarithmically with age and are two times higher in U.S. blacks than whites. Internationally, mortality rates are highest in U.S. blacks and in northern Europe and are lowest in Japan. It is projected that by the year 2000, a 90% increase in annual incidence of the disease and a 37% increase in annual mortality rates will be observed. Although prostate cancer may be a relatively indolent neoplasm in the elderly, the overall decrease in life span in patients with this disease is approximately 10 years. Adenocarcinoma of the prostate is the most common of the fatal pathophysiological prostate cancers, and most often involves a malignant transformation of epithelial cells in the peripheral region of the prostate gland.

Improvement in the treatment of prostate cancer has centered on early detection. In recent years, screening tests which detect certain proteins or peptides secreted by the prostate gland, i.e., markers, (e.g. prostate-specific antigen (PSA), prostatic acid phosphatase (PAP), prostatic inhibin (PIP)), have increased the power to diagnose this disease in asymptomatic patients.

Treatment of prostate cancer in men under the age of 65 has focused on radical surgery, e.g., prostatectomy, and/or radiotherapy, but the impact of these aggressive approaches on overall survival remains debatable. The approach to treatment of men over the age of 65 historically has been more conservative, and is based on the ablation or control of testosterone production. This result is usually achieved by surgical castration, by administration of pituitary gonadotropin inhibitors such as estrogens or luteinizing hormone releasing hormone (LHRH) analogues, or a combination of these treatment methods. Estrogens such as diethylstilbestrol are potent inhibitors of the release from the pituitary gland of luteinizing hormone (LH), the gonadotropin that regulates testosterone production, and consequently, estrogen administration can cause a fall in testosterone to castration levels. Maximum suppression of plasma testosterone is typically achieved by 3 mg/day of diethylstilbestrol. Other estrogens such as conjugated estrogens are about as equally effective in the lowering of the plasma level as diethylstilbestrol. However, diethylstilbestrol has a poor cardiovascular profile, and death from cardiovascular disease is not uncommon in patients treated with large doses of diethylstilbestrol. Thus, while dosages of up to 3 mg/day of diethylstilbestrol are typically safe, this treatment regime is not indicated for men with preexisting cardiovascular disease.

Prostatic carcinoma often metastasizes to the pelvis and lumbar vertebrae, causing bone loss and associated pain. Hormone manipulation often may result in significant palliation of metastatic prostate cancer, with improvement of bone pain and other disease-associated symptoms. Androgen ablation or control is, thus, also a major adjunctive therapy in advanced metastatic prostate cancer.

Despite initial improvement on hormonal treatment, a majority of patients with locally unresectable or metastatic disease will progress and fail to respond to further hormonal therapies. In this large group of patients, other forms of treatment are far less effective. Radiotherapy often may relieve the symptoms of bone pain, but is not curative. Over time, the disease will progress with a fatal outcome.

As noted hereinabove, prostatic hyperplasia is another common proliferative disease of the prostate gland. This disorder affects men over the age of 45 and increases in frequency with age. Prostatic hyperplasia begins in the periurethral region as a localized proliferation and progresses to compress the remaining normal gland. The hyperplasia can compress and obstruct the urethra. Treatment includes surgery, and administration of pituitary gonadotropin inhibitors and/or 5α-reductase enzyme inhibitors.

In another area of physiology and biochemistry, the vitamin D area, extensive research during the past two decades has established important biologic roles for vitamin D apart from its classic role in bone and mineral metabolism. Specific nuclear receptors for 1α,25-dihydroxyvitamin $D_3$, the hormonally active form of vitamin D, are present in cells from diverse organs not involved in calcium homeostasis. For example, Miller et al., 52 *Cancer Res.* (1992) 515–520, have demonstrated biologically active, specific receptors for 1,25-dihydroxyvitamin $D_3$ in the human prostatic carcinoma cell line, LNCaP.

It has been reported that certain vitamin D compounds and analogues are potent inhibitors of malignant cell proliferation and inducers/stimulators of cell differentiation. 1α,25-dihydroxyvitamin $D_3$ has been shown to regulate growth and promote the differentiation of many malignant cells. For example, U.S. Pat. No. 4,391,802 issued to Suda et al. discloses that 1α-hydroxyvitamin D compounds, specifically 1α,25-dihydroxyvitamin $D_3$ and 1α-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Antiproliferative and differentiating actions of 1α,25-dihydroxyvitamin $D_3$ and other vitamin $D_3$ analogues have been reported with respect to prostate cancer cell lines. More recently, an association between vitamin D receptor gene polymorphism and prostate cancer risk has been reported, suggesting that vitamin D receptors may have a role in the development, and possible treatment, of prostate cancer.

These previous studies have focused exclusively on vitamin $D_3$ compounds. Even though these compounds may indeed be highly effective in promoting differentiation in malignant cells in culture, their practical use in differentiation therapy as anticancer agents is severely limited because of their equally high potency as agents affecting calcium metabolism. At the levels required in vivo for effective use as antileukemic agents, these same compounds can induce markedly elevated and potentially dangerous blood calcium levels by virtue of their inherent calcemic activity. That is, the clinical use of 1α,25-dihydroxyvitamin $D_3$ and other vitamin $D_3$ analogues as anti-cancer agents is precluded, or severely limited, by the risk of hypercalcemia. This indicates a need for vitamin D therapies with greater specific activity and selectivity of action, i.e., vitamin D compounds and/or formulations with antiproliferative and differentiating effects but which have less calcemic activity. In particular, there is a need for vitamin D therapies that can be administered orally to provide the active vitamin D blood level necessary for antiproliferative and prodifferentiative effects without the risk of hypercalcemia. The need for such vitamin D therapies is no greater than in the treatment of prostate hyperplastic and neoplastic prostatic diseases.

BRIEF SUMMARY OF THE INVENTION

The present invention provides a method of treating prostatic disease conditions such as those characterized by hyperproliferative cell growth and/or abnormal cell differentiation, e.g., prostate cancer and prostatic hyperplasia. The method includes the administration of a delayed and/or sustained release vitamin D therapy to a subject suffering from such diseases to inhibit abnormal cell growth and promote cell differentiation. The delayed and/or sustained release vitamin D therapy includes 1α-hydroxyprevitamin D compounds and/or active vitamin D compounds in a delayed and/or sustained release formulation.

The foregoing, and other advantages of the present invention, are realized in one aspect thereof in a method of inhibiting the hyperproliferative activity of human prostatic cancer or hyperplastic cells, comprising treating the cells with an effective amount of a vitamin D therapy which is a delayed and/or sustained release vitamin D formulation. The treating step includes inhibiting proliferation of, and inducing and enhancing differentiation in such prostatic cells, and the preferred route of administration is oral. The sustained release vitamin D formulation includes 1α-hydroxyprevitamin D and/or an active vitamin D in a sustained release matrix. The delayed sustained release formulation further includes an enteric coat of the active ingredient(s).

Preferred among the 1α-hydroxyprevitamin D compounds for the sustained release or the delayed sustained release formulation in accordance with the present invention are 1α,25-dihydroxyprevitamin $D_3$, 1α,24-dihydroxyprevitamin $D_3$, 1α-hydroxyprevitamin $D_3$, 1α,25-dihydroxyprevitamin $D_2$, 1α,24-dihydroxyprevitamin $D_2$, 1α-hydroxyprevitamin $D_2$, 1α,25-dihydroxyprevitamin $D_4$, 1α,24-dihydroxyprevitamin $D_4$, and 1α-hydroxyprevitamin $D_4$. Preferred among the active vitamin D compounds are 1α,25-dihydroxyvitamin $D_3$, 1α,24-dihydroxyvitamin $D_3$, 1α-hydroxyvitamin $D_3$, 1α,25-dihydroxyvitamin $D_2$, 1α,24-dihydroxyvitamin $D_2$, 1α-hydroxyvitamin $D_2$, 1α,25-dihydroxyvitamin $D_4$, 1α,24-dihydroxyvitamin $D_4$, and 1α-hydroxyvitamin $D_4$.

The effective or therapeutic amount of the 1α-hydroxyprevitamin D compound, in unit dosage form, is 0.01 μg/kg/day to 2.0 μg/kg/day, and similarly, the amount of active vitamin D in delayed and/or sustained release form is 0.01 μg/kg/day to 2.0 μg/kg/day.

The invention further is a method of treating human prostate cancer, comprising administering to a male subject who has prostate cancer an effective amount of vitamin D compound which compound is 1α-hydroxyprevitamin D or an active vitamin D in delayed and/or sustained release form and which has a hypercalcemia risk substantially lower than that of 1α,25-dihydroxyvitamin $D_3$ administered, alone or in previously known formulations, to decrease or stabilize the cellular abnormal proliferative activity of the cancer. Thus, in addition to ameliorating prostatic conditions, the formulations of present invention overcome the inherent inadequacies of presently known oral vitamin D formulations, by providing a delayed and/or sustained release vitamin D oral medicament.

In one embodiment, the oral medicament is a sustained release (SR) vitamin D which includes a 1α-hydroxyprevitamin D compound or an active vitamin D compound in a sustained release matrix (hereinafter "SR pre D" and "SR active D," respectively). The 1α-hydroxyprevitamin D is preferably represented by formula (I) or (II) as defined hereinbelow. The compounds of formulas (I) and (II) include 1α-hydroxyprevitamin D, 1α,24-dihydroxyprevitamin D, and 1α,25-dihydroxyprevitamin D.

In accordance with the SR pre D formulation of the medicament of invention, i.e., 1α-hydroxyprevitamin D as the active ingredient, 1α-hydroxyprevitamin D acts as a prodrug for the active vitamin D to inhibit abnormal cell proliferation of and induce or enhance cell differentiation in prostatic diseases. The sustained increase in the blood level of the active 1α-hydroxyvitamin D or its metabolite provided by administration of 1α-hydroxyprevitamin D is achieved with significantly less hypercalcemia than that resulting from oral dosing of the 1α,25-dihydroxyvitamin $D_3$.

In the SR pre D, the 1α-hydroxyprevitamin D is provided in a form that remains relatively stable at room temperature, and is solvent-free. The 1α-hydroxyprevitamin D is then administered to an animal or human being in an oral dosage formulation. As the 1α-hydroxyprevitamin D is released from the oral dosage formulation, it is absorbed from the intestine. 1α-hydroxyprevitamin D is inactive, i.e., does not bind to the vitamin D receptor protein and does not stimulate intestinal calcium absorption. As the 1α-hydroxyprevitamin D is warmed by the core temperature of the animal or human being, it is thermally converted to the corresponding activated 1α-hydroxyvitamin D. The thermal conversion to the active form takes a sufficiently long period of time such that most of this conversion occurs in the time period after the 1α-hydroxyprevitamin D has been absorbed from the intestine of the animal or human being. Thus, the SR pre D produces a greater sustained blood level of the corresponding activated vitamin D with significantly less stimulation of intestinal calcium absorption than is obtained by administering orally the corresponding activated vitamin D itself.

In the SR active D formulation of the present invention, activated vitamin D is incorporated in sustained release matrix suitable for oral administration. That is, the activated vitamin D is formulated so that it is bound in a matrix which provides a sustained release when exposed to the contents of the intestine.

In a second embodiment, the oral composition of the present invention is a delayed and sustained release (DSR) vitamin D, e.g., a sustained release vitamin D with an enteric coating. The 1α-hydroxyprevitamin D or activated vitamin D-containing matrix is suitably covered with an enteric coating that is resistant to disintegration in gastric juices. The enteric coated, sustained release formulation of vitamin D, i.e., delayed sustained release vitamin D, (hereafter referred to as "DRS pre D" and "DSR activated or active D," respectively) is then administered orally to an animal or a human. As the DSR pre D or DSR activated D of the invention travels past the proximal portion of the small intestine, the enteric coating dissolves. The 1α-hydroxyprevitamin D or active vitamin D-containing matrix is exposed to intestinal fluids, and 1α-hydroxyprevitamin D or activated vitamin D is gradually released over a sustained period of time and absorbed from the intestine. Since the major portion of activated vitamin D of corresponding 1α-hydroxyvitamin from the hydroxylated previtamin is absorbed at a point beyond the proximal portion of the small intestine, a reduced stimulation of calcium uptake from the intestine occurs. This reduces the risk of hypercalcemia and hypercalciuria, thus increasing the therapeutic window. The gradual release also allows a greater sustained level of activated vitamin D compound in the serum to be obtained and, hence, provides a beneficial effect on diseased prostatic tissue.

The oral DSR composition of present invention may also suitably include a combination of activated previtamin D and activated vitamin D (hereafter referred to as "DSR activated pre D and D"). This embodiment of the invention includes one or more of the compounds of formulas (I), (II), (III), and/or (IV), defined hereinafter, contained in an enteric coated, sustained release formulation suitable for oral administration.

Thus, for treatment of prostatic diseases, e.g., prostatic cancer or hyperplasia, a subject is provided orally an effective amount of SR vitamin D which is 1α-hydroxyprevitamin D and/or active vitamin D in a sustained release matrix, or an effective amount of DSR activated vitamin D or DSR activated pre D, or an effective amount of DSR activated pre D and D, thereby increasing the blood level of activated vitamin D in an animal or human being, inhibiting prostatic cellular proliferation, and inducing or enhancing cell differentiation.

For treatment of prostate conditions in accordance with the present invention, SR vitamin D or DSR vitamin D is suitably administered alone as an active ingredient (i.e., as a first anticancer agent) or in a mixture including a second anticancer agent, an androgen ablation agent, a 5α-reductase inhibitor or combinations thereof.

In another aspect, the invention is a pharmaceutical composition which includes a first anticancer agent that is an SR vitamin D or a DSR vitamin D and an agent selected from the group consisting of (i) a second anticancer agent, (ii) a bone agent, (iii) an androgen ablation agent and (iv) a 5α-reductase inhibitor and combinations thereof, and a physiologically acceptable carrier. The active vitamin D compound is present in a dosage range of about 0.01 μg/kg/day to about 2.0 μg/kg/day; the active previtamin D is also present in a dosage range of 0.01 μg/kg/day to 2.0 μg/kg/day.

Other advantages and a fuller appreciation of specific adaptations, compositional variations, and physical attributes will be gained upon an examination of the following detailed description of preferred embodiments, taken in conjunction with the figures of the drawing and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which:

FIG. 1 is a graph of the time course conversion of certain 1α-hydroxyprevitamins to the vitamin form; and FIG. 2 is a graph of the expected results of active vitamin D concentration versus time after administration of DSR activated D.

DETAILED DESCRIPTION OF THE INVENTION

Figure 1:
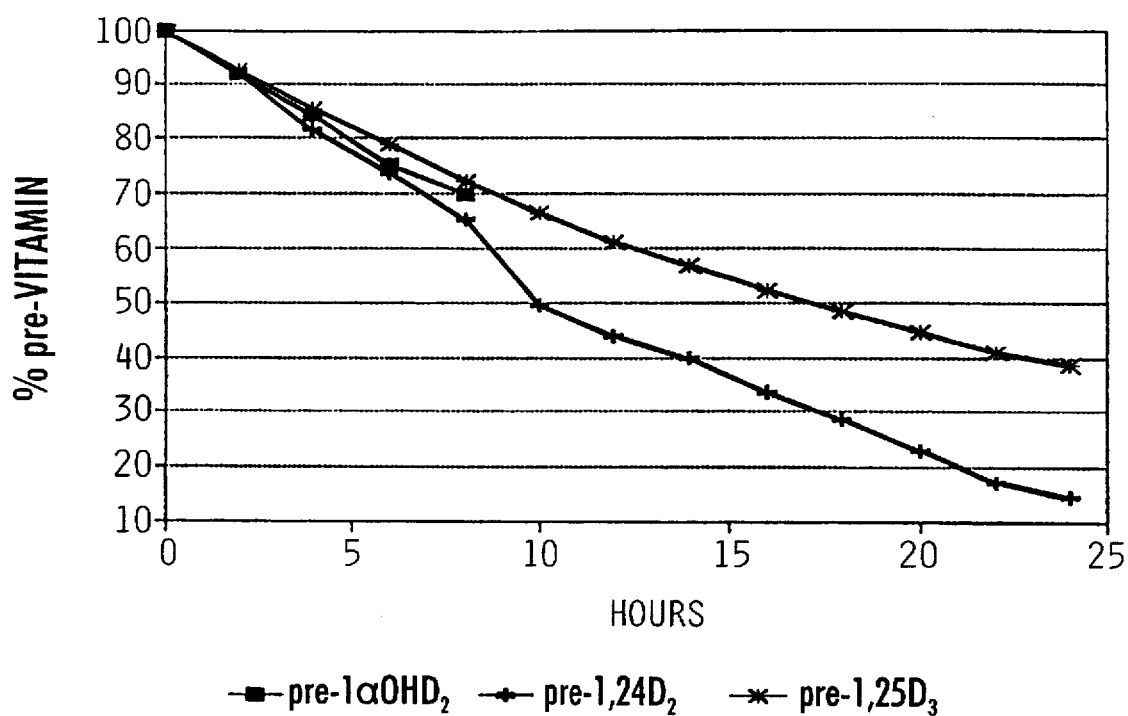

The present invention provides an effective method for the treatment of neoplastic and hyperplastic diseases. Particularly, the present invention relates to therapeutic methods for inhibiting, ameliorating or alleviating the hyperproliferative cellular activity of diseases of the prostate, e.g., prostatic cancer and prostatic hyperplasia. The present invention provides a novel treatment for a patient suffering from a hyperproliferative disease such as prostatic cancer or prostatic hyperplasia which includes administering a medicament that is 1α-hydroxyprevitamin D or a DSR active vitamin D or active previtamin D. The medicament is provided to the patient without causing dose-limiting hypercalcemia and hypercalciuria, i.e., unphysiologically high and deleterious blood calcium levels and urine calcium levels, respectively. These attributes are achieved through certain chemical and physical properties of the compositions of the present invention.

In accordance with the invention, when effective amounts of SR vitamin D or DSR vitamin D therapies are administered to patients with prostatic cancer or prostatic hyperplasia, the proliferative activity of the abnormal prostatic cells is inhibited or alleviated, and cell differentiation is induced or promoted, with significantly less hypercalcemia and hypercalciuria than is observed after the same amount of activated vitamin D is administered in previously known formulations. Thus, the medicament of the present invention has an improved therapeutic index. The effective amounts of active ingredient in SR and DSR formulations for treatment of prostatic neoplastic and hyperplastic conditions ranges from about 0.01 μg/kg/day to about 2.0 μg/kg/day for 1α-hydroxyprevitamin D, and 0.01 μg/kg/day to 2.0 μg/kg/day for active vitamin D.

It is known that vitamin $D_3$ must be hydroxylated in the C-1 and C-25 positions before it is activated, i.e., before it will produce a biological response. A similar metabolism appears to be required to activate other forms of vitamin D, e.g., vitamin $D_2$ and vitamin $D_4$. Therefore, as used herein, the term "activated vitamin D" or "active vitamin D" are intended to refer to a vitamin D compound or analogue that has been hydroxylated in at least the C-1 position of the A ring of the molecule and binds or is converted/metabolizes to a compound that binds the vitamin D receptor (VDR). In other words, as to the latter, a 1α-hydroxyvitamin D is further hydroxylated to a compound which is then capable of binding the VDR. Similarly, the term "activated previtamin D" refers to a previtamin D compound that has been hydroxylated in at least the C-1 position of the A ring and is converted/metabolizes to a compound that binds the VDR.

Also, as used herein, the term "lower" as a modifier for alkyl or acyl is meant to refer to a straight or branched hydrocarbon chain having 1 to 4 carbon atoms. Specific examples of such hydrocarbon chains are methyl, ethyl, propyl, butyl, isobutyl, t-butyl, ethenyl, propenyl, butenyl, isobutenyl, isopropenyl, formyl, acetyl, propionyl or butyryl. The term "aromatic acyl" is meant to refer to an unsubstituted benzoyl group or substituted benzoyl group such as nitrobenzoyl or dinitrobenzoyl. The term "treat" or "treatment" is meant to refer to alleviation, amelioration, repair or prevention of prostatic diseases as well as inhibition of cellular abnormal or hyperproliferation, and promotion, inducement and/or enhancement of cell differentiation.

The 1α-hydroxyprevitamin D compounds and active vitamin D compounds in SR and DSR form of the present invention are those that have effective antiproliferative and cell differentiation activity (i.e., reversal of malignant transformation), particularly with respect to cells of prostatic diseases, e.g., prostatic cancer and prostatic hyperplasia, but have a lower tendency or inability to cause the undesired side effects of hypercalcemia and/or hypercalciuria. In other words, the compositions or medicaments of the present invention act as antiproliferative agents and cell differentiation agents when exposed to malignant or other hyperproliferative cells without significantly altering calcium metabolism. The delayed and sustained release action of the formulations of the present invention make them useful and preferred agents for safely inhibiting hyperproliferation and achieving malignant cell differentiation. The formulations of the present invention, thus, overcome the shortcomings of the known active vitamin D formulations mentioned above, and can be considered preferred agents for the control and treatment of malignant diseases such as prostate cancer as well as benign prostatic hyperplasia.

The preferred embodiments of the compositions or medicaments of present invention used in the therapeutic methods for ameliorating certain prostatic conditions are described herein as follows.

A first embodiment of the medicament of present invention is an SR formulation which includes substantially pure 1α-hydroxyprevitamin D or an active vitamin D contained in a sustained release matrix. It has been found that when substantially pure 1α-hydroxyprevitamin D is administered orally, it produces a greater sustained increase in the blood level of activated vitamin D and significantly less hypercalcemia and hypercalciuria than the same amount of activated vitamin D administered orally in previously known formulations. 1α-Hydroxyprevitamin D is, therefore, useful in the treatment of prostatic conditions. As used herein, the term "substantially pure" means at least 85% pure 1α-hydroxyprevitamin D. The term "sustained" as used herein means a blood level which remains relatively constant (i.e., ±10 pg/ml or ±10% of the mean value) for a period greater than a defined period, i.e., typically greater than 4 hours.

It is known that vitamin $D_3$ is synthesized endogenously in the skin of animals and man from 7-dehydrocholesterol by an ultraviolet-mediated photochemical reaction which breaks the B ring of the 7-dehydrocholesterol between carbon-4 and carbon-9 to form previtamin $D_3$. The triene previtamin $D_3$ is unstable and over time thermally converts to vitamin $D_3$. At normal body temperature an equilibrium exists between previtamin $D_3$ and vitamin $D_3$, as seen below.

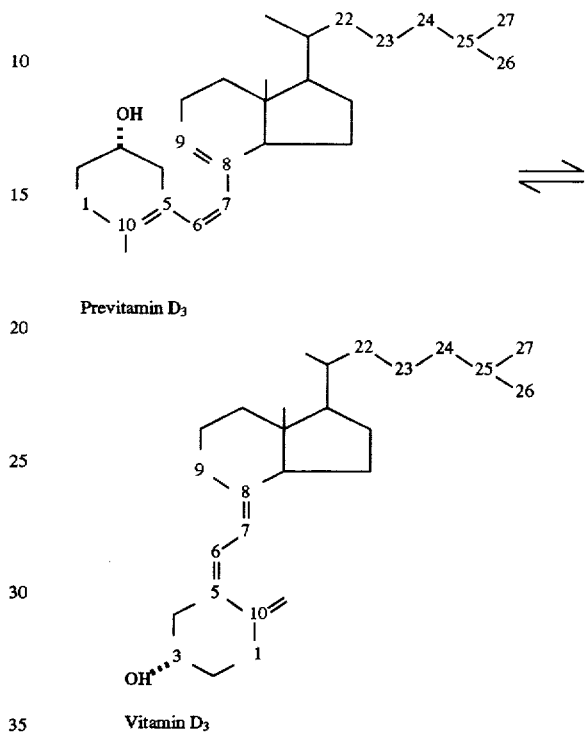

As vitamin $D_3$ is further metabolized in vivo this equilibrium shifts to the vitamin $D_3$ form. A similar conversion and equilibrium state exists for 1α-hydroxyprevitamin D.

The 1α-hydroxyprevitamin D of the present invention preferably has the general formula (I):

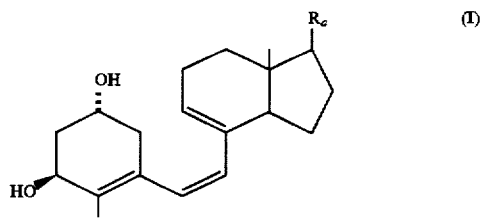

wherein $R_a$ is a side chain having at least 7 carbon atoms, and can be branched or unbranched, saturated or unsaturated, hetero-substituted or nonhetero-substituted, cyclic or noncyclic, and wherein the thermal isomer of the 1α-hydroxyprevitamin D of the general formula (I) is an active vitamin D and increases the serum calcium of the vitamin D-deficient rat as determined by standard methods used by biochemists in the vitamin D area.

Among the preferred 1α-hydroxyprevitamin D of this embodiment of the present invention are those having the formula (II):

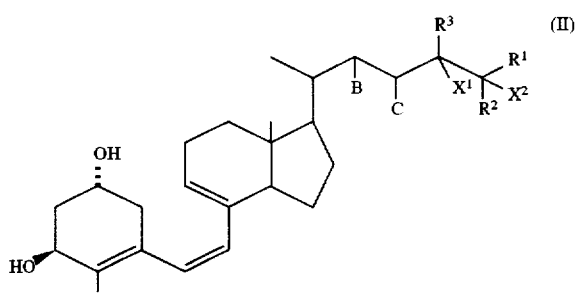

wherein B and C are either hydrogen or a carbon—carbon bond forming a double bond between C-22 and C-23; $R^1$ and $R^2$ are each independently hydrogen, hydroxy, fluoro, lower alkyl, lower fluoroalkyl, O-lower alkyl, lower alkenyl, lower fluoroalkenyl, O-lower alkenyl, O-lower acyl, O-aromatic acyl, lower cycloalkyl, or taken together with the carbon to which they are binded, form a $C_3$–$C_8$ cyclocarbon ring; $R^3$ is hydrogen, fluoro, lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl; and $X^2$ is hydrogen, hydroxyl, or, taken with $R^1$ or $R^2$, constitutes a double bond. Preferred among the compounds of formula (II), i.e., preferred 1α-hydroxy-previtamin D compounds, are:

1α,25-dihydroxyprevitamin $D_3$ [1α,25-(OH)$_2$preD$_3$];
1α,24,25-trihydroxyprevitamin $D_3$ [1α,24,25-(OH)$_3$preD$_3$];
1α-hydroxyprevitamin $D_3$ [1α-(OH)preD$_3$];
1α,24-dihydroxyprevitamin $D_3$ [1α,24-(OH)$_2$preD$_3$];
1α,24-dihydroxy-25-fluoro-previtamin $D_3$ [1α,24-(OH)$_2$-25-FpreD$_3$];
1α,25-dihydroxyprevitamin $D_2$ [1α,25-(OH)$_2$preD$_2$];
1α,24,25-trihydroxyprevitamin $D_2$ [1α,24,25-(OH)$_3$preD$_2$];
1α-hydroxyprevitamin $D_2$ [1α-(OH)preD$_2$];
1α,24-dihydroxyprevitamin $D_2$ [1α,24-(OH)$_2$preD$_2$];
1α,24-dihydroxy-25-fluoro-previtamin $D_2$ [1α,24-(OH)$_2$-25-FpreD$_2$];
1α,25-dihydroxyprevitamin $D_4$[1α,25-(OH)$_2$preD$_4$];
1α,24,25-trihydroxyprevitamin $D_4$[1α,24,25-(OH)$_3$preD$_4$];
1α-hydroxyprevitamin $D_4$[1α-(OH)preD$_4$];
1α,24-dihydroxyprevitamin $D_4$[1α,24-(OH)$_2$preD$_4$]; and
1α,24-dihydroxy-25-fluoro-previtamin $D_4$1α,24-(OH)$_2$-25-FpreD$_4$].

Among those compounds of formula (II) that have a chiral center in the side chain, e.g., at C-24, it is understood that both epimers (e.g., R and S) and the racemic mixture are within the scope of the present invention.

In a preferred embodiment, the compounds of formulas (I) or (II) are provided in a substantially pure, crystalline, solvent-free form. As such the 1α-hydroxyprevitamin D remains quite stable at room temperature with minimal conversion to the 1α-hydroxyvitamin D form. The compounds of formulas (I) or (II), i.e., 1α-hydroxyprevitamin D, can be readily manufactured in crystalline form according to the procedure described in Vandewalle et al. U.S. Pat. No. 4,539,153.

The 1α-hydroxyprevitamin D compounds of this embodiment can be processed in accordance with conventional methods of pharmacy to produce medicinal agents for administration to patients, e.g., mammals, including human beings. For example, dosage forms of the compounds of formulas (I) or (II) with conventional excipients, include admixtures suitable for oral administration. Dosage forms of the 1α-hydroxyprevitamin D can be combined with any nontoxic pharmaceutically acceptable carrier, such as cornstarch, lactose, or sucrose, which does not deleteriously react with the active compounds. The formulation can be produced in tablet, capsule, powders, troches and lozenges. Whatever method of formulation is used, care should be taken to avoid extended exposure to solvents and heat as under such conditions there will be a tendency for a portion of 1α-hydroxyprevitamin D to convert to the 1α-hydroxyvitamin D form. Because heat and dissolution are preferably avoided, the preferred method of tablet formulation is the method known as dry granulation, i.e., the 1α-hydroxyprevitamin D is solvent-free and heat stable at room temperature.

The 1α-hydroxyprevitamin D is administered to the animal or human in oral dosage formulation. As the 1α-hydroxyprevitamin D is released from the oral dosage formulation, it is absorbed from the intestine. 1α-Hydroxyprevitamin D does not interact with the vitamin D receptor protein of the enterocytes and, therefore, does not stimulate intestinal calcium absorption.

It is also known that the binding of activated vitamin D with the vitamin D receptor protein of the enterocyte induces the release of enzymes which degrade a significant portion of the unbound activated vitamin D present in the intestine. Such degradation decreases the amount of activated vitamin D available for absorption into the blood stream. Since 1α-hydroxyprevitamin D does not bind with the vitamin D receptor protein there is no such enzyme induction. Thus, less degradation occurs in the intestine and a greater amount is available for absorption into the blood stream than is the case with the corresponding activated vitamin D.

As the 1α-hydroxyprevitamin D is warmed by the core temperature of the animal or human being, it is thermally converted to the corresponding activated vitamin D. The reaction time for thermal conversion to the active form is sufficiently long so that most of the conversion occurs over time after the 1α-hydroxyprevitamin D has been absorbed. Thus, the 1α-hydroxyprevitamin D oral dosage formulation produces a greater sustained blood level of the corresponding activated vitamin D with significantly less stimulation of intestinal calcium absorption than is possible with a comparable oral dosage amount of the activated vitamin D itself. Thus, oral administration of 1α-hydroxyprevitamin D provides greater sustained blood levels of active vitamin D for treatment of prostatic neoplastic and hyperplastic cells without significant calcemic activity than with comparable oral administration of the active vitamin D itself.

The active vitamin D of the SR formulation of the medicament of the present invention is preferably a 1α-hydroxyvitamin D having the general formula (III):

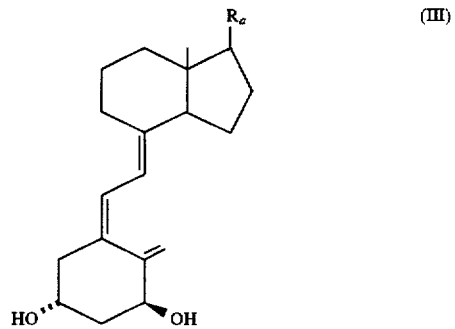

wherein $R_a$ is a side chain having at least 7 carbon atoms, and can be branched or unbranched, saturated or unsaturated, hetero-substituted or nonhetero-substituted, cyclic or noncyclic, or any vitamin D compound or homologue which binds with the vitamin D receptor protein.

Among the preferred 1α-hydroxyvitamin D compounds of this embodiment of the present invention are those having the formula (IV):

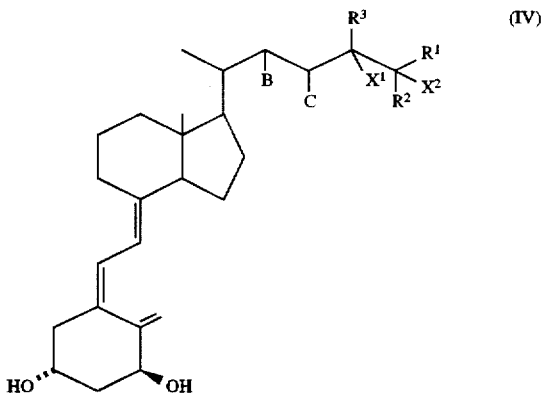

wherein B and C are either hydrogen or a carbon—carbon bond forming a double bond between C-22 and C-23; $R^1$ and $R^2$ are each independently hydrogen, hydroxy, fluoro, lower alkyl, lower fluoroalkyl, O-lower alkyl, lower alkenyl, lower fluoroalkenyl, O-lower alkenyl, O-lower acyl, O-aromatic acyl, lower cycloalkyl, or taken together with the carbon to which they are binded, form a $C_3$–$C_8$ cyclocarbon ring; $R^3$ is hydrogen, fluoro; lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl; and $X^2$ is hydrogen, hydroxyl, or, taken with either $R^1$ or $R^2$, constitutes a double bond. Preferred among the compounds of formula (IV), i.e., the preferred 1α-hydroxyvitamin D compounds, are:

1α,25-dihydroxyvitamin $D_3$ [1α,25-$(OH)_2D_3$];
1α,24,25-trihydroxyvitamin $D_3$ [1α,24,25-$(OH)_3D_3$];
1α-hydroxyvitamin $D_3$ [1α-$(OH)D_3$];
1α-hydroxy-25-fluoro-vitamin $D_3$ [1α-(OH)-25-$FD_3$]
1α,24-dihydroxyvitamin $D_3$ [1α,24-$(OH)_2D_3$];
1α,24-dihydroxy-25-fluoro-vitamin $D_3$ [1α,24-$(OH)_2$-25-$FD_3$];
1α,25-dihydroxyvitamin $D_2$ [1α,25-$(OH)_2D_2$];
1α,24,25-trihydroxyvitamin $D_2$ [1α,24,25-$(OH)_3D_2$];
1α-hydroxyvitamin $D_2$ [1α-$(OH)D_2$];
1α-hydroxy-25-fluoro-vitamin $D_2$ [1α-(OH)-25-$FD_2$]
1α,24-dihydroxyvitamin $D_2$ [1α,24-$(OH)_2D_2$];
1α,24-dihydroxy-25-fluoro-vitamin $D_2$ [1α,24-$(OH)_2$-25-$FD_2$];
1α,25-dihydroxyvitamin $D_4$ [1α,25-$(OH)_2D_4$];
1α,24,25-trihydroxyvitamin $D_4$ [1α,24,25-$(OH)_3D_4$];
1α-hydroxyvitamin $D_4$ [1α-$(OH)D_4$];
1α-hydroxy-25-fluoro-vitamin $D_4$ [1α-(OH)-25-$FD_4$];
1α,24-dihydroxyvitamin $D_4$ [1α,24-$(OH)_2D_4$]; and
1α,24-dihydroxy-25-fluoro-vitamin $D_4$ [1α,24-$(OH)_2$-25-$FD_4$].

Among those active vitamin D compounds that have a chiral center in the side chain, e.g., 1α,24-dihydroxyvitamin $D_2$, it is understood that both epimers (e.g., R and S) and the racemic mixture are within the scope of the present invention.

The compounds of formula (III) and (IV) of this embodiment can be processed in accordance with conventional methods of pharmacy to produce sustained release medicinal agents (more specifically described below) for administration to patients, e.g., mammals, including humans. For example, dosage forms of the compounds of formulas (III) and (IV) with conventional excipients, include admixtures suitable for oral administration. Dosage forms of the 1α-hydroxyvitamin D can be combined with any nontoxic pharmaceutically acceptable carrier, such as cornstarch, lactose, or sucrose, which does not deleteriously react with the active compounds. The SR formulation can be produced in tablet or capsule form.

A very preferred formulation of this embodiment is a matrix which binds the 1α,25-dihydroxyvitamin $D_3$ along with an acceptable pharmaceutical excipient and which permits a slow, relatively steady release of the 1,25-dihydroxyvitamin $D_3$ over a period of four to eight hours.

The means for providing sustained (i.e., controlled) release of the active ingredient may be selected from any of the known sustained-release delivery systems for controlling the release of an active ingredient over a course of about four or more hours including the wax matrix system, and the Eudragit RS/RL system (of Rohm Pharma, GmbH, Weiterstadt, Germany).

The wax matrix system disperses the active ingredient(s) in a wax binder which slowly dissolves in body fluids to gradually release the active ingredient(s).

The preferred controlled-release oral drug delivery system is the Eudragit RL/RS system in which the active ingredient, activated vitamin D, is combined with a sustained release matrix, and sprayed into granules having a dimension of 25/30 mesh. The granules are then uniformly coated with a thin polymeric lacquer which is water insoluble but slowly water permeable. The coated granules can be mixed with optional additives such as antioxidants, stabilizers, binder, lubricant, processing aids and the like. The mixture may be compacted into a tablet which, prior to use, is hard and dry or it may be poured into a capsule. After the tablet or capsule is swallowed and comes into contact with the aqueous intestinal fluids, the thin lacquer begins to swell and slowly allows permeation of intestinal fluids. As the intestinal fluid slowly permeates the lacquer coating, the active ingredients are slowly released. By the time the tablet has passed through the intestinal tract, about four to eight hours, the active ingredients will have been slowly but completely released. Accordingly, the ingested tablet will effect a sustained release of the activated vitamin D as well as any other active ingredient.

The Eudragit system is comprised of high permeability lacquers (RL) and low permeability lacquers (RS). The permeability of the coating and thus the time course of drug release can be titrated by varying the proportion of RS to RL coating material.

For further details of the Eudragit RL/RS system, reference is made to technical publications available from Rohm Tech, Inc. 195 Canal Street, Maiden, Mass., 02146. See also, K. Lehmann, D. Dreher "Coating of tablets and small particles with acrylic resins by fluid bed technology," *Int. J. Pharm. Tech. & Prod. Mfr.* 2(r), 31–43 (1981).

In the second embodiment of the medicament or composition of the present invention, one or more of activated vitamin D compounds or one or more substantially pure 1α-hydroxyprevitamin D or combinations thereof are included in an enteric coated, sustained release formulation. In other words, an enteric coated, sustained release formulation is a delayed, sustained (DSR) formulation of the compounds of formula (I) and (II), or (III) and (IV) or combinations thereof.

Surprisingly, it has been found that the DSR activated D formulation of the invention significantly increases the therapeutic window of the activated vitamin D compound. That is, the risk of hypercalcemia and hypercalciuria is significantly decreased and the therapeutic effectiveness is significantly increased for the activated vitamin D when orally administered in the DSR activated D formulation as compared to the same amount of activated vitamin D orally administered in heretofore known oral formulations of those compounds. Furthermore, the DSR activated D formulation permits a higher sustained blood level of the activated vitamin D to be obtained than was possible with previously known oral formulations of the activated vitamin D compound.

To prepare the DSR formulations of this embodiment of the medicament of the present invention, the coated granules of formulas (I), (II), (III) or (IV), described hereinbefore, are either formed into a tablet or put into a capsule, and the tablet or capsule is coated with an enteric-coating material which dissolves at a pH of 6.0 to 7.0 to form the DSR formulation. One such pH dependent enteric-coating material is Eudragit L/S which dissolves in intestinal fluid but not in the gastric juices. Other enteric-coating materials may be used such as cellulose acetate phthalate (CAP) which is resistant to dissolution by gastric juices but readily disintegrates due to the hydrolytic effect of the intestinal esterases.

The particular choice of enteric-coating material is not of significance as long as a sustained or controlled release over a period of 4 to 8 hours is obtained and release is delayed until the DSR formulation reaches the intestine. Although not essential to the invention, it is preferred that release is delayed until the DSR formulation has reached beyond the proximal part of the small intestine.

Those skilled in the art will also appreciate that the formulations of the present invention may also be encapsulated in other time-release delivery systems such as a liposome delivery system, polysaccharides exhibiting a slow release mechanism, salistic or other polymer implants or microspheres. In such time release delivery systems, the active compound is suitably protected with differentially degradable coatings, e.g., by microencapsulation, multiple coatings, etc., and such means effect continual dosing of compositions contained therein.

While the preferred embodiments are described above, it should be understood that the only limitation as to the kind of active vitamin D compound used in this invention is that the vitamin D compound itself or its in vivo metabolite binds with the vitamin D receptor protein. The only limitation as to the 1α-hydroxyprevitamin D is that it converts thermally to an active vitamin D compound in which it or its in vivo metabolite binds with the VDR.

The compounds of 1α-hydroxyprevitamin D and active vitamin D, preferably of formulas (I), (II),(III) and (IV), are useful as active compounds in the pharmaceutical compositions of the above described embodiments. Such compositions suitably may include physiologically acceptable excipients or vehicles. These pharmaceutical compositions constitute another aspect of the invention. The dosage forms may also contain adjuvants, such as preserving or stabilizing adjuvants.

As noted hereinbefore, the pharmacologically active compounds of this invention can be processed in accordance with conventional methods of pharmacy to produce medicinal agents for administration to patients, e.g., mammals including humans. For example, the compounds of formulas (I) or (II) can be employed in admixtures with conventional excipients, e.g., pharmaceutically acceptable carrier substances suitable for enteral (e.g., oral) or parenteral application which do not deleteriously react with the active compounds.

Suitable pharmaceutically acceptable carriers for compounds of formulas (III) and (IV) include but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc. The compounds of formulas (I) and (II) should, on the other hand, be formulated as substantially solvent-free.

For oral application, particularly suitable are tablets, dragees, lozenges, powders, or capsules as described hereinbefore. A sweetener can be used if a sweetened vehicle is desired. Generally, for treatment of prostatic hyperproliferative diseases, the compositions of this invention are dispensed in dosages comprising about 0.1 µg/kg/day to about 2.0 µg/kg/day for 1α-hydroxyprevitamin D and about 0.1 µg/kg/day to 2.0 µg/kg/day for active vitamin D with a pharmaceutically acceptable carrier in a suitable matrix and/or enteric coated in accordance with the embodiments of the present invention.

It will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on the age, body weight, general state of health, on the diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

The compositions in accordance with the present invention may also contain other therapeutically valuable substances or may contain more than one of the compounds specified herein and in the claims in admixture. Advantageously, the compounds of formulas (I), (II), (III) and (IV) or combinations thereof together with other therapeutic agents can be orally administered in accordance with the above described embodiments in dosage amounts of 0.1 to 2.0 µg per day for 1α-hydroxyprevitamin D and 0.1 µg to 2.0 µg/day for active vitamin D.

Included within the scope of the present invention is the co-administration of effective dosages of the antihyperproliferative compounds of the present invention in SR or DSR form with known androgen ablation or control agents or testosterone level lowering agents such as estrogens (e.g., diethylstilbestrol), LHRH analogues, and 5α-reductase enzyme inhibitors such as finasteride, antiestrogens (e.g., Tamoxifen™), and antiandrogens (e.g., flutamide). (See, e.g., U.S. Pat. No. 5,372,996, incorporated herein by reference.) It is anticipated that a symbiotic effect is obtainable with these various combinations, and will provide an increased therapeutic effect. Also, there is the potential to provide therapy wherein the adverse side effects with some of these agents, e.g., the deleterious cardiovascular effects of estrogen, are considerably reduced compared to when these agents are used alone in larger dosages. Possible dose ranges of these co-administered androgen-control or testosterone level-lowering agents are 0.002 to 0.20 µg/kg/day.

Further included within the scope of the present invention is the co-administration of effective dosages of the 1α-hydroxyprevitamin D or the active vitamin D in the DSR or SR formulations of the present invention as first anticancer agents with a second anticancer agent, e.g., a cytotoxic agent, particularly in metastatic prostate cancer wherein relapse has occurred following hormonal treatment. Such agents may suitably include estramustine phosphate, prednimustine, cisplatin, 5-fluoro-uracil, melphalan, hydroxyurea, mitomycin, idarubicin, methotrexate, adriamycin and daunomycin. It is anticipated that an active vitamin D of formula (III) or (IV) or a 1α-hydroxyprevitamin D of formula (I) or (II) used in combination with various anticancer drugs can give rise to a significantly enhanced cytotoxic effect on cancerous cells, thus providing an increased therapeutic effect. Specifically, as a significantly increased growth inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered second anticancer agents are 0.1 to 1 µg/kg/day.

Also included within the scope of the present invention is the co-administration of effective dosages of the compound of formulas (I), (II), (III) or (IV) with other hormones or agents, e.g., estrogens, which are known to ameliorate bone diseases or disorders. It is noted above that prostate cancer often metastasizes to bone, causing bone loss and associated pain. Such bone agents may include conjugated estrogens or their equivalents, calcitonin, bisphosphonates, calcium supplements, cobalamin, pertussis toxin and boron. Possible dose ranges for these co-administered agents are provided in Table 1.

TABLE 1

Possible Oral Dose Ranges for Various Agents
Co-Administered With 1α-Hydroxyvitamin D of Formula (I)

| Agent | Dose Ranges | | |
|---|---|---|---|
| | Broad | Preferred | Most Preferred |
| Conjugated Estrogens or Equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Bisphosphonates (mg/day) | 0.50–20 | 1–15 | 5–10 |
| Calcium Supplements (mg/day) | 250–2500 | 500–1500 | 750–1000 |
| Cobalamin (µg/day) | 5–200 | 20–100 | 30–50 |
| Pertussis Toxin (mg/day) | 0.1–2000 | 10–1500 | 100–1000 |
| Boron (mg/day) | 0.10–3000 | 1–250 | 2–100 |

Antiestrogens such as Tamoxifen™ are also known bone agents which may be used in conjunction with the compounds and compositions of the present invention.

The embodiments of the present invention are further explained by the following examples which should not be construed by way of limiting the scope of the present invention. In the following examples, high pressure liquid chromatography (HPLC) was performed on a Waters Chromatograph, using a Zorbax Sil ODS column.

Time Course of 1α-hydroxyprevitamin D Conversion to 1α-hydroxyvitamin D

EXAMPLE 1

1α-OH-D$_2$, 1α,24-(OH)$_2$preD$_2$ and 1α,25-(OH)$_2$D$_3$

A series of experiments were conducted which address the in vitro conversion of previtamin to vitamin for three 1α-hydroxyprevitamin D's: 1α-hydroxyprevitamin D$_2$, 1α,24-dihydroxyprevitamin D$_2$ and 1α-hydroxyprevitamin D$_3$. Each 1α-hydroxyprevitamin D was dissolved in ethanol, incubated at 37° C. in a water bath, and samples taken at two-hour intervals. An analytical HPLC separation was performed on each sample to quantify the thermal conversion of the previtamin to the vitamin form. The data collected were normalized to account for the presence of any vitamin form in the initial formulation (≦10%). The results are presented in FIG. 1 which is a plot of % previtamin versus time in hours. Linear regression lines were generated for each previtamin. From these, the half-life of thermal conversion, i.e., the time for 50% of the previtamin to thermally convert to the vitamin form, was determined as follows:

| | |
|---|---|
| 1α-hydroxyprevitamin D$_2$ | 12.9 h |
| 1α,24-dihydroxyprevitamin D$_2$ | 12.2 h |
| 1α,25-dihydroxyprevitamin D$_3$ | 17.7 h |

These data indicate that at normal body temperature, the 50% conversion of 1α-hydroxylated previtamin D to 1α-hydroxylated vitamin in vitro is greater than 12 hours. In vivo, one would expect a similar rate of conversion. Thus, contrary to conventional wisdom, 1α-hydroxyprevitamins have a rate of conversion suitable for an oral medication formulation.

Bioavailability and Pharmacokinetic Testing of 1α-hydroxyprevitamin D

EXAMPLE 2

1α,24-(OH)$_2$preD$_2$

An experiment was conducted which assessed the oral bioavailability of 1α,24-dihydroxyprevitamin D$_2$ ("1,24-(OH)$_2$preD$_2$"). In this experiment, normal rats maintained on a normal diet were assigned randomly to treatment and control groups. The rats were orally administered single doses of 1α,24-(OH)$_2$preD$_2$ in a fractionated coconut oil (FCO) (1.5 µg, which was approximately 7.5 µg/kg). The control group received only the vehicle. For both groups, blood was obtained at 6 hours postdosing and analyzed for serum levels of the vitamin form, 1α,24-dihydroxyvitamin D$_2$.

The data are summarized in Table 2 below.

TABLE 2

Serum Levels of 1α,24-dihydroxyvitamin D$_2$ (1α,24-(OH)$_2$D$_2$) in Rats At 6 Hours After Single Oral Doses of 1α,24-dihydroxyprevitamin D$_2$ (1α,24-(OH)$_2$preD$_2$)

| Test Compound | Dose (µg) | n | Serum 1α,24-(OH)$_2$D$_2$ (pg/mL)* |
|---|---|---|---|
| Vehicle | 0.000 | 5 | 13.8 ± 4.2 |
| 1α,24-(OH)$_2$preD$_2$ | 1.5 | 5 | 65.5 ± 10.1 |

*values are mean ± SD

These data confirm that orally administered 1α,24-(OH)$_2$preD$_2$ is bioavailable, as evidenced by increased circulating 1α,24-(OH)$_2$D$_2$. These results are surprising and unexpected.

EXAMPLE 3

1α,25-(OH)$_2$preD$_3$

Male weanling rats are fed a diet deficient in vitamin D and with normal calcium (0.47%). After a period of four weeks has elapsed, the rats are divided into two groups, and orally administered either 1α,25-(OH)$_2$preD$_3$ (0.25 µg/kg) in a vehicle such as lactose or the vehicle (control) alone. Four hours after administration, the rats are killed and their blood level of 1α,25-(OH)$_2$D$_3$ is measured using a standard technique.

Following this procedure demonstrates that the blood level of 1α,25-(OH)$_2$D$_3$ in rats that are administered 1α,25-(OH)$_2$preD$_3$ is significantly elevated over the blood level of control animals.

EXAMPLE 4

1α,25-(OH)$_2$preD$_3$

Male weanling rats are fed a vitamin D-deficient diet containing normal Ca (0.47%) and P (0.3%). After four weeks on this diet, the rats are separated into seventeen groups and orally administered either 1α,25-(OH)$_2$D$_3$ or 1α,25-(OH)$_2$preD$_3$ in a vehicle such as lactose or the vehicle alone (control). One group is killed 8 hours after dosing with the vehicle. Eight groups are orally administered a single dose of either 1α,25-(OH)$_2$preD$_3$ or 1α,25-(OH)$_2$D$_3$ and killed at 2, 4, 6, 9, 12, 18, 24, and 48 hours after dosing. The blood is collected and analyzed for 1α,25-(OH)$_2$D$_3$ levels.

The results demonstrate that dosing with 1α,25-(OH)$_2$preD$_3$ results in increased 1α,25-(OH)$_2$D$_3$ serum levels. The results further demonstrate that the increase in serum 1α,25-(OH)$_2$D$_3$ is more gradual and sustained for a greater duration than the 1α,25-(OH)$_2$D$_3$ pharmacokinetics observed after dosing with 1α,25-(OH)$_2$D$_3$.

EXAMPLE 5

Comparison of Bioavailability-1α,25-(OH)$_2$preD$_3$ v. 1α,25-(OH)$_2$D$_3$

Three-week-old rats were maintained on a vitamin D-deficient diet containing normal levels of calcium and phosphorus for 3–6 weeks until marked hypocalcemia was observed. The rats then were assigned randomly to treatment groups and were orally administered single doses of 1α,25-(OH)$_2$preD$_3$ or 1α,25-(OH)$_2$D$_3$ in a fractionated coconut oil (0.255 µg, which was approximately 1.5 µg/kg). A control group received only the vehicle. For all treatment groups, blood was obtained at 12 hours postdosing, and analyzed for serum levels of the vitamin form.

The data are summarized in Table 3 below.

TABLE 3

Serum Levels of 1α,25-dihydroxyvitamin D$_3$ (1α,25-(OH)$_2$D$_3$) in Rachitic Rats at 12 Hours After Single Oral Doses of 1α,25-dihydroxyprevitamin D$_3$ (1α,25-(OH)$_2$preD$_3$)

| Test Compound | Dose (µg) | n | Serum 1α,25-(OH)$_2$—D$_3$ (pg/mL ± SD) |
|---|---|---|---|
| Vehicle | 0.000 | 8 | 14.7 ± 5.1 |
| 1a,25-(OH)$_2$preD$_3$ | 0.255 | 6 | 615.4 ± 298.1** |
| 1a,25-(OH)$_2$D$_3$ | 0.255 | 6 | 326.8 ± 192.0 |

**p < 0.01 relative to 1α,25-(OH)$_2$D$_3$

These data show that oral 1α,25-(OH)$_2$preD$_3$ produced significantly more serum 1α,25-(OH)$_2$D$_3$ than oral 1α,25-(OH)$_2$D$_3$. These data confirm that orally administered 1α,25-(OH)$_2$preD$_3$ is bioavailable, as evidenced by increased circulating 1α,25-(OH)$_2$D$_3$. They also show that 1α,25-(OH)$_2$preD$_3$ has greater bioavailability than the active form of the vitamin, 1α,25-(OH)$_2$D$_3$.

VDR Binding Analyses

EXAMPLE 6

1α,25-(OH)$_2$preD$_3$

The VDR binding affinity of 1α,25-(OH)$_2$preD$_3$ was compared to that of 1α,25-(OH)$_2$D$_3$, its active vitamin form.

1α,25-(OH)$_2$preD$_3$ or 1α,25-(OH)$_2$D$_3$ were incubated with the vitamin D receptor protein and tracer amounts of $^3$H-1α,25-(OH)$_2$D$_3$ under standard conditions for a competitive binding assay. The amount of 1α,25-(OH)$_2$preD$_3$ and 1α,25-(OH)$_2$D$_3$ competitor was varied between 7.8 and 1000 pg or 1.0 and 25 pg, respectively.

Concurrent with the incubations for binding, a tube of 1α,25-(OH)$_2$preD$_3$ was incubated at the same temperature and for the same length of time to assess the amount of 1α,25-(OH)$_2$preD$_3$ that had equilibrated to the vitamin form. HPLC analysis indicated that at the end of the incubation period approximately 2% of the 1α,25-(OH)$_2$preD$_3$ had equilibrated to the vitamin form. The level of binding of the 1α,25-(OH)$_2$preD$_3$ form was corrected for the amount of the vitamin form that had been generated during the assay procedure. The results of the binding analyses are given in Table 4.

TABLE 4

Binding of 1α,25-dihydroxyprevitamin D$_3$ to Vitamin D Receptor in vitro

| Amount 1,25-preD$_3$ (pg/tube) | Total Detectable Binding (pg/tube) | Corrected Binding (pg/tube) |
|---|---|---|
| 7.8 | ND | ND |
| 15.6 | ND | ND |
| 31.3 | ND | ND |
| 62.5 | 1.88 | 0.6 |
| 125 | 3.02 | 0.5 |
| 250 | 6.32 | 1.3 |
| 500 | 12.0 | 2.0 |
| 1000 | 20.5 | 0.5 |

The data shown in Table 4 above show that the 1α,25-(OH)$_2$preD$_3$ has little or no affinity for the VDR, i.e., has an affinity for the receptor less than 0.01 of the affinity of the 1α,25-(OH)$_2$D$_3$, thus 1α,25-(OH)$_2$preD$_3$ must equilibrate to the 1α,25-(OH)$_2$D$_3$ form before it is biologically active.

EXAMPLE 7

1α,24-(OH)$_2$preD$_2$

A comparison of VDR binding affinities between 1α,24-(OH)$_2$preD$_2$ and its vitamin form, 1α,24-(OH)$_2$D$_2$, is conducted as described in Example 6. The results show that 1α,24-(OH)$_2$preD$_2$ has substantially less affinity for the receptor than does its vitamin form, 1α,24-(OH)$_2$D$_2$.

EXAMPLE 8

1α,24-(OH)$_2$preD$_4$

A comparison of VDR binding affinities between 1α,24-(OH)$_2$preD$_4$ and its vitamin form, 1α,24-(OH)$_2$D$_4$, is conducted as described in Example 6. The results show that 1α,24-(OH)$_2$preD$_4$ has substantially less affinity for the receptor than does its vitamin form, 1α,24-(OH)$_2$D$_4$.

Acute Hypercalcemia Testing of 1α-hydroxyprevitamin D

EXAMPLE 9

1α,25-(OH)$_2$preD$_3$

Male weanling rats are fed a vitamin D-deficient diet containing normal Ca (0.47%) and P (0.3%). After approximately 4–6 weeks on this diet, the rats are separated into five groups and orally administered either 1α,25-dihydroxyvitamin $D_3$ (0.06 or 0.12 µg/kg/day) or 1α,25-dihydroxyprevitamin $D_3$ (0.06 or 0.12 µg/kg/day) in a vehicle such as lactose, or the vehicle alone (control), for 3 days. All animals are exsanguinated 24 hours after the last dose and the blood is analyzed for serum calcium and serum phosphorus. The results demonstrate that dosing with 1α,25-dihydroxyvitamin $D_3$ causes a greater rise in serum calcium and serum phosphorus than comparable dosing with 1α,25-dihydroxyprevitamin $D_3$.

Bioavailability and Pharmacokinetic Testing of Delayed, Sustained Release Form of Active Vitamin D (DSR Active Vitamin D)

EXAMPLE 10

Formulation With Equal Parts Eudragit L100 and S100 and Testing Thereof

An appropriate amount of activated vitamin D was dissolved in ethanol and combined with the matrix components listed in Table 4 and sprayed onto 850 g 25/30 mesh nonpareil beads. After drying, the beads were coated with the enteric coat also listed in Table 5.

TABLE 5

| Component | Ingredient | Amount (g) |
|---|---|---|
| Matrix | Eudragit RS100 | 50 |
| | Methanol | 50 |
| | Ethanol with drug | |
| | Distilled water | 5 |
| | Acetone | qs to 500 |
| Enteric coat | ATEC (acetyl triethyl citrate, a plasticizer) | 54 |
| | Methanol | 600 |
| | Distilled water | 30 |
| | Eudragit L100 | 153 |
| | Eudragit S100 | 153 |
| | Talc | 40 |
| | Acetone | qs to 4000 |

After formulation the beads (500 mg/capsule) were packaged in #0 gelatin capsules for administration to dogs.

Dogs (Beagles, males and females, 13 kg and 9 kg, respectively) were administered 5 capsules/day of formulation (DSR-008). Blood was drawn for baseline determination, 24 hours after dosing but prior to subsequent dosing, and the serum calcium determined. Dose administration was terminated after 2 days with serum calcium levels significantly above normal.

Five capsules/day of the above formulation (DSR-008) were administered to a female dog for 7 days. The normal serum calcium range in female dogs is 10.0 to 12.4 mg/dl with a mean of 11.2 mg/dl. The serum calcium at baseline of this experiment was 11.7 mg/dl; the subsequent values on successive days were as follows: 12.1, 12.3, 12.7, 13.1, 13.5, and 15.1 mg/dL.

These results demonstrate that the biological activity of the active vitamin D in this DSR formulation is revealed over a sustained period.

EXAMPLE 11

Formulation With Unequal Amounts Eudragit L100 and S90, and Testing Thereof

An appropriate amount of activated vitamin D was dissolved in ethanol and combined with the matrix components listed in Table 6 and sprayed onto 850 g 25/30 mesh nonpariel beads. After drying, the beads were coated with the enteric coat also listed in Table 6.

TABLE 6

| Component | Ingredient | Amount (g) |
|---|---|---|
| Matrix | Eudragit RS100 | 10 |
| | Methanol | 10 |
| | Ethanol with drug | |
| | Distilled water | 1 |
| | Acetone | qs to 100 |
| Enteric coat | ATEC (acetyl triethyl citrate, a plasticizer) | 68 |
| | Methanol | 750 |
| | Distilled water | 35 |
| | Eudragit L100 | 338 |
| | Eudragit S90 | 49 |
| | Talc | 50 |
| | Acetone | qs to 5000 |

After formulation the beads (500 mg/capsule) are packaged in #0 gelatin capsules for administration to dogs.

Dogs (as in Example 10) were administered 5 capsules/day of formulation (DSR-010). Blood was drawn for baseline determination, 24 hours after dosing but prior to subsequent dosing, and the serum calcium determined. Dose administration was terminated after 2 days with serum calcium levels significantly above normal.

Five capsules/day of the above formulation (DSR-010) were administered to a female dog for 2 days. The normal serum calcium range in female dogs is 10.0 to 12.4 mg/dl with a mean of 11.2 mg/dl. The serum calcium at baseline was 10.9; the subsequent values on successive days were as follows: 13.8 and 16.1 mg/dl.

These data show that the active vitamin D in this DSR formulation is readily bioavailable.

EXAMPLE 11

Formulation With Stearic Acid Matrix, and Testing Thereof

An appropriate amount of activated vitamin D was dissolved in ethanol and combined with the matrix components listed in Table 7 and sprayed onto 850 g 25/30 mesh nonpareil beads. After drying, the beads were coated with the enteric coating also listed in Table 7.

TABLE 7

| Component | Ingredient | Amount (g) |
|---|---|---|
| Matrix | Stearic acid | 10 |
| | Ethanol with drug | |
| | Acetone | qs to 90 |
| Enteric coat | ATEC (acetyl triethyl citrate, a plasticizer) | 68 |
| | Methanol | 750 |
| | Distilled water | 35 |
| | Eudragit L100 | 338 |
| | Eudragit S90 | 49 |
| | Talc | 50 |
| | Acetone | qs to 5000 |

After formulation the beads (500 mg/capsule) are packaged in #0 gelatin capsules for administration to dogs.

Dogs (as in Example 10) were administered 5 capsules/day of formulation (DSR-012). Blood was drawn for baseline determination, 24 hours after dosing but prior to subsequent dosing, and the serum calcium determined. Dose administration was terminated after 2 days with serum calcium levels significantly above normal.

Five capsules/day of the above formulation (DSR-012) were administered to a male dog for 2 days. The normal serum calcium range in male dogs at this facility is 10.6 to 12.0 mg/dl with a mean of 11.3 mg/dl. The serum calcium at baseline was 11.4 mg/dl; the subsequent values on successive days were as follows: 14.2 and 15.5 mg/dl.

These data illustrate that the active vitamin D in this DSR formulation is readily bioavailable.

EXAMPLE 13

DSR 1α,25-(OH)$_2$D$_3$

A dog receives a capsule of 1α,25-dihydroxyvitamin D$_3$ drug formulated as illustrated in this invention (DSR). Another dog receives a similar amount of the 1α,25-dihydroxyvitamin D$_3$ in fractionated coconut oil (FCO). Blood is drawn at 0, 0.5, 1, 1.5, 2, 3, 4, 6, 9, 15, 24, 36, and 72 hours after dose administration. The blood is analyzed for active vitamin D levels. The animal administered the drug in the capsule formulation shows a slower rise in blood concentration of active vitamin D, a lower maximum concentration of active vitamin D in the blood and prolonged elevation of active vitamin D blood level relative to the animal receiving the drug in fractionated coconut oil.

Figure 2:
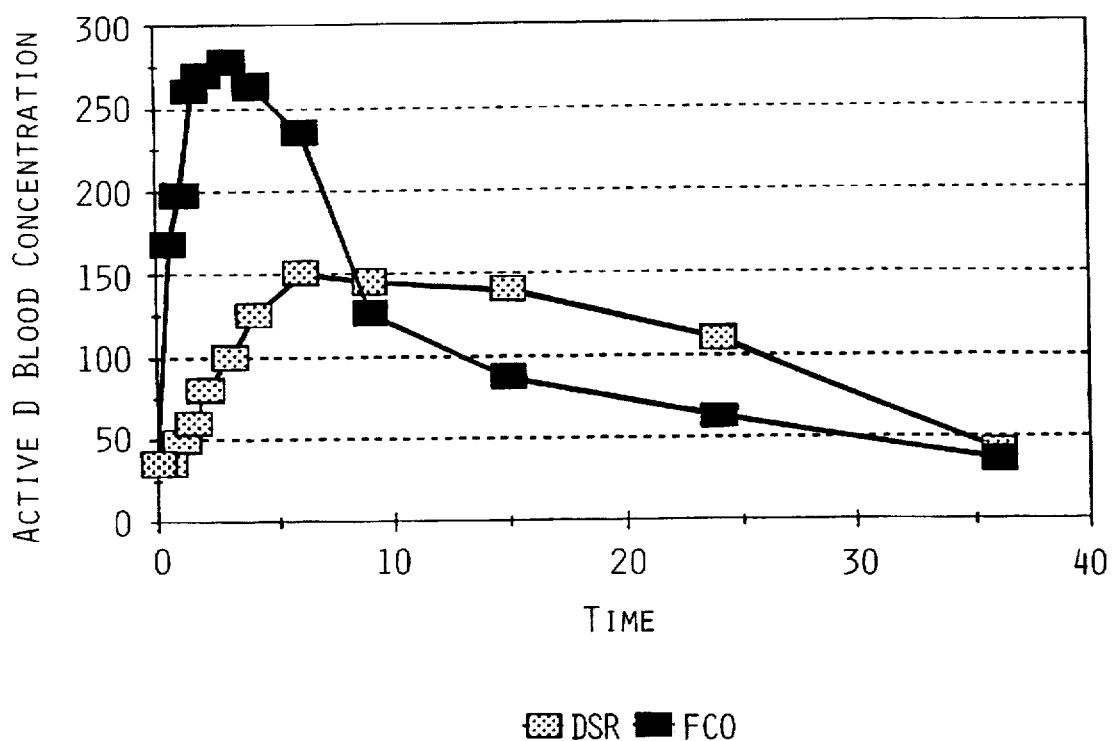

The graph of FIG. 2 depicts the blood levels of active vitamin D expected from the above example.

These procedures demonstrate that dosing animals with the formulation described in accordance with the present invention results in 1α,25-dihydroxyvitamin D$_3$ serum levels with a slower rise and longer duration than the 1α,25-dihydroxyvitamin D$_3$ pharmacokinetics observed after dosing with 1α,25-dihydroxyvitamin D$_3$ in fractionated coconut oil.

EXAMPLE 14

Delayed and Sustained Levels of Active Vitamin D in Serum

Patients are administered two micrograms of 1α,25-(OH)$_2$D$_3$ formulated as described in this invention. Blood samples collected 0, 2, 6, 8, and 12 hours after dose administration are analyzed for 1α,25-(OH)$_2$D$_3$ levels. The results indicate that the levels of 1α,25-(OH)$_2$D$_3$ at 2, 6, and 8 hours are increased over the level at 0, but are below levels considered to cause hypercalcemia. These results indicate a delayed and sustained release of 1α,25-(OH)$_2$D$_3$.

EXAMPLE 15

Acute Hypercalcemia Testing

Patients are administered 2.0 micrograms of calcitriol formulated as described in this invention once daily for 7 days. An overnight urine collection after the last dose, and blood drawn 24 hours after the last dose are analyzed for calcium content. No hypercalcemia or hypercalciuria is observed, indicating low toxicity.

Prostate Cell VDR Binding of Active Vitamin D

EXAMPLE 16

1α,24-(OH)$_2$D$_2$

VDR binding of vitamin D compounds by prostate cells is demonstrated using the techniques of Skowronski et al., 136 *Endocrinology* (1995) 20–26, which is incorporated herein by reference. Prostate-derived cell lines are cultured to near confluence, washed and harvested by scraping. Cells are washed by centrifugation, and the cell pellet resuspended in a buffered salt solution containing protease inhibitors. The cells are disrupted by sonication while cooling on ice. The supernatant obtained from centrifuging the disrupted cells at 207,000×g for 35 min at 4° C. is assayed for binding. 200 μL of soluble extract, (1–2 mg protein/ml supernatant) is incubated with a 1 nM $^3$H-1α,25-(OH)$_2$D$_3$ and increasing concentrations of 1α,24-(OH)$_2$-D$_2$ (0.01–100 nM) for 16–20 hrs at 4° C. Bound and free hormones are separated with hydroxylapatite using standard procedures. Specific binding is calculated by subtracting nonspecific binding obtained in the presence of a 250-fold excess of nonradioactive 1α,25-(OH)$_2$D$_3$ from the total binding measured. The results demonstrate that 1α,24-(OH)$_2$D$_2$ has strong affinity for prostate VDR, indicating that 1α,24-(OH)$_2$D$_2$ has potent biological activity in respect of prostate cells.

EXAMPLE 17

1α,24-(OH)$_2$D$_4$

The procedure of Example 16 is repeated using the active vitamin D analogue 1α,24-dihydroxyvitamin D$_4$, and the specific binding is determined. The results demonstrate that 1α,24-(OH)$_2$D$_4$ has strong affinity for prostate VDR, indicating that 1α,24-(OH)$_2$D$_2$ has potent biological activity in respect of prostate cells.

EXAMPLE 18

1α,25-(OH)$_2$D$_4$

The procedure of Example 16 is repeated using the active vitamin D analogue 1α,25-dihydroxyvitamin D$_4$, and the specific binding is determined. The results demonstrate that 1α,25-(OH)$_2$D$_4$ has strong affinity for prostate VDR, indicating that 1α,25-(OH)$_2$D$_2$ has potent biological activity in respect of prostate cells.

Inhibition of Prostate Cell Proliferation by Active Vitamin D

EXAMPLE 19

1α,24-(OH)$_2$D$_2$

Inhibition of cell proliferation is demonstrated using the techniques of Skowronski et al., 132 *Endocrinology* (1993) 1952–1960 and 136 *Endocrinology* (1995) 20–26, both of which are incorporated herein by reference. The cell lines, LNCaP and PC-3, which are derived from human prostate adenocarcinoma, are seeded in six-well tissue culture plates at a density of about 50,000 cells/plate. After the cells have attached and stabilized, about 2–3 days, the medium is replenished with medium containing vehicle or the active vitamin D analogue, 1α,24-(OH)$_2$D$_2$, at concentrations from $10^{-11}$ to $10^{-7}$M. Medium containing test analogue or vehicle is replaced every three days. After 6–7 days, the medium is removed, and the cells are rinsed, precipitated with cold 5% trichloroacetic acid, and washed with cold ethanol. The cells are solubilized with 0.2N sodium hydroxide, and the amount of DNA determined by standard procedures. The results show that cultures incubated with 1α,24-(OH)$_2$D$_2$ in accordance with the present invention have significantly fewer cells than the control cultures.

EXAMPLE 20

1α,24-(OH)$_2$D$_4$

The procedure of Example 19 is repeated using the active vitamin D analogue 1α,24-(OH)$_2$D$_4$, and the cell number is determined. Cultures incubated with $1\alpha,24\text{-}(OH)_2D_4$ have significantly fewer cells than the control cultures.

EXAMPLE 21

$1\alpha,25\text{-}(OH)_2D_4$

The procedure of Example 19 is repeated using the active vitamin D analogue $1\alpha,25\text{-}(OH)_2D_4$, and the cell number is determined. Cultures incubated with $1\alpha,25\text{-}(OH)_2D_4$ have significantly fewer cells than the control cultures.

Stimulation of Prostate Cell Differentiation by Active Vitamin D

EXAMPLE 22

$1\alpha,24\text{-}(OH)_2D_2$

Using the techniques of Skowronski et al., 132 *Endocrinology* (1993) 1952–1960 and 136 *Endocrinology* (1995) 20–26, both of which are incorporated herein by reference, cells of the cell line, LNCaP, which is derived from a human metastatic prostate adenocarcinoma and known to express PSA, are seeded in six-well tissue culture plates at a density of about 50,000 cells/plate. After the cells have attached and stabilized, about 2–3 days, the medium is replenished with medium containing vehicle or the active vitamin D analogue, $1\alpha,24\text{-}(OH)_2D_2$, at concentrations from $10^{-11}$ to $10^{-7}$M. After 6–7 days, the medium is removed and stored at $-20°$ C. for prostate specific antigen (PSA) analysis.

The cells are rinsed, precipitated, and the amount of DNA determined by standard procedures. The cells are resuspended, and the cell number determined. PSA is measured by standard known methods. Cultures incubated with $1\alpha,24\text{-}(OH)_2D_2$ have significantly more PSA than control cultures when expressed as mass of PSA/cell.

EXAMPLE 23

$1\alpha,24\text{-}(OH)_2D_4$

The procedure of Example 22 is repeated except the active vitamin D analogue is $1\alpha,24\text{-}(OH)_2D_4$. The PSA is measured and cultures incubated with $1\alpha,24\text{-}(OH)_2D_4$ have significantly more PSA than control cultures when expressed as mass of PSA/cell.

EXAMPLE 24

$1\alpha,25\text{-}(OH)_2D_4$

The procedure of Example 22 is repeated except the active vitamin D analogue is $1\alpha,25\text{-}(OH)_2D_4$. The PSA is measured and cultures incubated with $1\alpha,25\text{-}(OH)_2D_4$ have significantly more PSA than control cultures when expressed as mass of PSA/cell.

Clinical Studies

EXAMPLE 25

$1\alpha,24\text{-}(OH)_2preD_2$

Patients with advanced androgen-independent prostate cancer participate in an open-labeled study of $1\alpha,24\text{-}(OH)_2preD_2$. Qualified patients are at least 40 years old, exhibit histologic evidence of adenocarcinoma of the prostate, and present with progressive disease which had previously responded to hormonal intervention(s). On admission to the study, patients begin a course of therapy with oral $1\alpha,24\text{-}(OH)_2preD_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral $1\alpha,24\text{-}(OH)_2preD_2$ is determined by administering progressively higher dosages to successive groups of patients. All doses are administered in the morning before breakfast. The first group of patients is treated with 25 µg of $1\alpha,24\text{-}(OH)_2preD_2$. Subsequent groups of patients are treated with 50, 75 and 100 µg/day. Dosing is continued uninterrupted for the duration of the study unless serum calcium exceeds 11.6 mg/dL or other toxicity of grade 3 or 4 is observed, in which case dosing is held in abeyance until resolution of the observed toxic effect(s) and then resumed at a level which has been decreased by 10.0 µg.

Results from the first phase of the study show that the MTD for $1\alpha,24\text{-}(OH)_2preD_2$ is above 20.0 µg/day, a level which is 10- to 40-fold higher than can be achieved with $1\alpha,25\text{-}(OH)_2D_3$. Analysis of blood samples collected at regular intervals from the participating patients reveal that the levels of circulating $1\alpha,24\text{-}(OH)_2D_2$ increase proportionately with the dosage administered, rising to maximum levels well above 100 pg/mL at the highest dosages, and that circulating levels of $1\alpha,25\text{-}(OH)_2D_3$ are suppressed, often to undetectable levels. Serum and urine calcium are elevated in a dose responsive manner. Patients treated with the MTD of $1\alpha,24\text{-}(OH)_2preD_2$ for at least six months report that bone pain associated with metastatic disease is significantly diminished.

During the second phase, patients are treated with $1\alpha,24\text{-}(OH)_2preD_2$ for 24 months at 0.5 and 1.0 times the MTD. After two years, CAT scans, x-rays and bone scans used for evaluating the progression of metastatic disease show stable disease or partial remission at the lower dosage, and partial or complete remission at the higher dosage.

EXAMPLE 26

DSR $1\alpha,25\text{-}(OH)_2D_2$

The study of Example 25 is repeated for the active vitamin D compound, $1\alpha,25\text{-}(OH)_2D_2$ in DSR form. The results of the phase one study indicate that patients treated with the MTD of DSR $1\alpha,25\text{-}(OH)_2D_2$ for at least six months report that bone pain associated with metastatic disease is significantly diminished. The results of the phase two study indicate that after two years, CAT scans, x-rays and bone scans used for evaluating the progression of metastatic disease show stable disease or partial remission at the lower dosage, and partial or complete remission at the higher dosage.

In summary, the present invention provides methods for treating prostatic diseases such as prostate cancer and prostatic hyperplasia by administration of an oral SR or DSR formulation of $1\alpha$-hydroxyprevitamin D or activated vitamin D or combinations thereof. The formulations of the present invention significantly reduce the risk of hypercalcemia and hypercalciuria associated with heretofore known formulations of activated vitamin D. Furthermore, the formulation of the invention produces higher levels of activated vitamin D for a greater sustained time per administration than is obtained with heretofore known oral formulations of activated vitamin D, resulting in improved blood levels of active vitamin D reaching the diseased prostate cells.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method of inhibiting the hyperproliferative cellular activity of human prostatic cancer or hyperplasia, comprising administering to a subject suffering therefrom and having a stomach and a small intestine, an effective amount of an oral medicament including a vitamin D compound which is 1α-hydroxyprevitamin D or an active vitamin D contained in a matrix, said matrix having means for releasably binding and controllably releasing said active vitamin D over a sustained period of time.

2. The method of claim 1, wherein said oral medicament further comprises an enteric coating which prevents release of said vitamin D compound, said coating being resistant to dissolution in the stomach but predisposed to dissolution in the intestine so as to prevent release of said vitamin D compound until said medicament is in the intestine.

3. The method of claim 2, wherein the small intestine has proximal, middle and distal portions, and said enteric coating is further resistant to dissolution in the proximal portion of the intestine but predisposed to dissolution in the middle and distal portion of the intestine so as to prevent release of said vitamin D compound until said medicament has traveled to the middle portion of the intestine.

4. The method of claim 2, wherein said enteric coating is resistant to dissolution in an environment having a pH less than 6.0.

5. The method of claim 3, wherein said enteric coating is resistant to dissolution in an environment having a pH less than 6.0.

6. The method of claim 1, wherein said 1α-hydroxyprevitamin D is 1α,25-dihydroxyprevitamin $D_3$, 1α,24-dihydroxyprevitamin $D_3$, 1α-hydroxyprevitamin $D_3$, 1α,25-dihydroxyprevitamin $D_2$, 1α,24-dihydroxyprevitamin $D_2$, 1α-hydroxyprevitamin $D_2$, 1α,24-dihydroxyprevitamin $D_4$, 1α,25-dihydroxyprevitamin $D_4$ or 1α-hydroxyprevitamin $D_4$.

7. The method of claim 1, wherein said active vitamin D is 1α,25-dihydroxyvitamin $D_3$, 1α,24-dihydroxyvitamin $D_3$, 1α-hydroxyvitamin $D_3$, 1α,25-dihydroxyvitamin $D_2$, 1α,24-dihydroxyvitamin $D_2$, 1α-hydroxyvitamin $D_2$, 1α,24-dihydroxyvitamin $D_4$, 1α,25-dihydroxyvitamin $D_4$ or 1α-hydroxyvitamin $D_4$.

8. A method for the treatment of prostatic diseases characterized by abnormal cell differentiation or cell proliferation, comprising administering to a male human in need of such treatment an effective proliferation-inhibiting amount of an oral medicament which is 1α-hydroxyprevitamin D compound or a vitamin D compound contained in a matrix, said vitamin D compound being an active vitamin D or a 1α-hydroxyprevitamin D, said matrix having means for releasably binding and controllably releasing said vitamin D compound over a sustained period of time.

9. The method of claim 8, wherein said proliferation-inhibiting amount of 1α-hydroxyprevitamin D is 0.01 µg/kg/day to 2.0 µg/kg/day.

10. The method of claim 8, wherein said proliferation-inhibiting amount of active vitamin D is 0.01 µg/kg/day to 2.0 µg/kg/day.

11. A method of treating human prostate cancer, comprising administering to a male subject who has prostate cancer an effective amount of a composition having a first anticancer agent which is 1α-hydroxyprevitamin D, a sustained release form of an active vitamin D compound or a delayed, sustained release form of an active vitamin D compound.

12. The method of claim 11, wherein said composition has a hypercalcemia risk substantially lower than that of 1α,25-dihydroxyvitamin $D_3$.

13. The method of claim 11, wherein said composition is administered in a mixture including a second anticancer agent selected from the group consisting of estramustine phosphate, prednimustine, cisplatin, 5-fluoro-uracil, melphalan, hydroxyurea, mitomycin, idarubicin, methotrexate, adriamycin and daunomycin.

14. The method of claim 13, wherein said second anticancer drug is present in the mixture in the range of about 0.002 to 0.02 µg/kg/day.

15. A pharmaceutical composition, comprising (a) a first anticancer agent which is a vitamin D compound selected from the group consisting of a 1α-hydroxyprevitamin D, an SR active vitamin D, DSR active vitamin D, and combinations thereof; and (b) an agent selected from the group consisting of (i) a second anticancer agent, (ii) a bone agent, (iii) an androgen control agent, (iv) a 5α-reductase inhibitor and combinations thereof.

16. The pharmaceutical composition of claim 15, wherein said active vitamin D compound is selected from the group consisting of 1α,25-dihydroxyvitamin $D_3$, 1α,24-dihydroxyvitamin $D_3$, 1α-hydroxyvitamin $D_3$, 1α,25-dihydroxyvitamin $D_2$, 1α,24-dihydroxyvitamin $D_2$, 1α-hydroxyvitamin $D_2$, 1α,24-dihydroxyvitamin $D_4$, 1α,25-dihydroxyvitamin $D_4$ and 1α-hydroxyvitamin $D_4$.

17. The pharmaceutical composition of claim 15, wherein said 1α-hydroxyprevitamin D compound is selected from the group consisting of 1α,25-dihydroxyprevitamin $D_3$, 1α,24-dihydroxyprevitamin $D_3$, 1α-hydroxyprevitamin $D_3$, 1α,25-dihydroxyprevitamin $D_2$, 1α,24-dihydroxyprevitamin $D_2$, 1α-hydroxyprevitamin $D_2$, 1α,24-dihydroxyprevitamin $D_4$, 1α,25-dihydroxyprevitamin $D_4$ and 1α-hydroxyprevitamin $D_4$.

18. The pharmaceutical composition of claim 15, wherein said second anticancer agent is selected from the group consisting of estramustine phosphate, prednimustine, cisplatin, 5-fluoro-uracil, melphalan, hydroxyurea, mitomycin, idarubicin, methotrexate, adriamycin and daunomycin.

19. The pharmaceutical composition of claim 15, wherein said active vitamin D compound is present in a dosage range of about 0.01 µg/kg/day to about 2.0 µg/kg/day.

20. The pharmaceutical composition of claim 15, wherein said 1α-hydroxyprevitamin D compound is present in a dosage range of about 0.01 µg/kg/day to about 2.0 µg/kg/day.

21. The pharmaceutical composition of claim 15, wherein said androgen control agent is selected from the group consisting of an estrogen, LHRH analogue, an antiestrogen and an antiandrogen.

22. The pharmaceutical composition of claim 15, wherein said 5α-reductase enzyme inhibitor is finasteride.

23. The pharmaceutical composition of claim 15, wherein said bone agent is selected from the group consisting of a conjugated estrogen, an antiestrogen, calcitonin, sodium fluoride, a bisphosphonate, a calcium supplement, cobalamin, pertussis toxin and boron.

24. A method of treating a human to alleviate the hyperproliferative cellular activity of prostatic cancer or hyperplasia, comprising administering to a male human in need thereof a therapeutically effective amount of 1α-hydroxyprevitamin D or active vitamin D in a formulation which is a sustained release form or a delayed, sustained release form, to decrease or stabilize prostate cancer or hyperplasia cellular activity and to effect a decreased risk of hypercalcemia.

* * * * *